(12) United States Patent
Fujimura

(10) Patent No.: US 9,510,731 B2
(45) Date of Patent: Dec. 6, 2016

(54) ULTRASOUND ENDOSCOPE AND ULTRASOUND BALLOON FOR ENDOSCOPE

(71) Applicant: OLYMPUS CORPORATION, Tokyo (JP)

(72) Inventor: Takanao Fujimura, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/637,531

(22) Filed: Mar. 4, 2015

(65) Prior Publication Data
US 2015/0173590 A1  Jun. 25, 2015

Related U.S. Application Data

(63) Continuation of application No. PCT/JP2014/061982, filed on Apr. 30, 2014.

(30) Foreign Application Priority Data

Aug. 22, 2013 (JP) ................. 2013-172473

(51) Int. Cl.
*A61B 1/00* (2006.01)
*A61B 8/12* (2006.01)
*A61B 8/00* (2006.01)

(52) U.S. Cl.
CPC ....... *A61B 1/00082* (2013.01); *A61B 1/00073* (2013.01); *A61B 1/00101* (2013.01); *A61B 8/12* (2013.01); *A61B 8/445* (2013.01)

(58) Field of Classification Search
CPC ............ A61B 1/00082; A61B 1/00073; A61B 1/00101; A61B 8/445

USPC ........................................................ 600/466
See application file for complete search history.

(56) References Cited

U.S. PATENT DOCUMENTS

| 4,466,443 | A | 8/1984 | Utsugi |
| 5,125,411 | A | 6/1992 | Yokoi et al. |
| 6,142,945 | A | 11/2000 | Sakamoto et al. |
| 2007/0232922 | A1* | 10/2007 | Kohno .................. A61B 1/018 600/459 |

(Continued)

FOREIGN PATENT DOCUMENTS

| EP | 0 062 315 A1 | 10/1982 |
| JP | 57-168648 A | 10/1982 |

(Continued)

*Primary Examiner* — Katherine Fernandez
*Assistant Examiner* — Katherine McDonald
(74) *Attorney, Agent, or Firm* — Scully, Scott, Murphy & Presser, P.C.

(57) ABSTRACT

An ultrasound endoscope includes an insertion portion that is inserted into a subject, an ultrasound transducer portion that is arranged at a distal end portion of the insertion portion and includes an ultrasound transmitting and receiving surface for transmitting and receiving ultrasound, a first balloon groove that is a groove formed between the insertion portion and the ultrasound transducer portion and is for locking a balloon that covers the ultrasound transmitting and receiving, a distal end face that is arranged on a distal end side with respect to the ultrasound transducer portion and is disposed spaced apart from the ultrasound transmitting and receiving surface, and a convex portion that is provided on the distal end face and on which stress concentrates when a finger is slid on the distal end face.

2 Claims, 12 Drawing Sheets

(56) References Cited

U.S. PATENT DOCUMENTS

2009/0247880 A1* 10/2009 Naruse ............... A61B 1/00082
　　　　　　　　　　　　　　　　　　　600/463

FOREIGN PATENT DOCUMENTS

| JP | 04-126138 A | 4/1992 |
| JP | 07-155326 A | 6/1995 |
| JP | 07-227393 A | 8/1995 |
| JP | 08-252255 A | 10/1996 |
| JP | 11-276487 A | 10/1999 |
| JP | 2000-116655 A | 4/2000 |
| JP | 2003-169804 A | 6/2003 |
| JP | 2012-249739 A | 12/2012 |

* cited by examiner

ULTRASOUND ENDOSCOPE AND ULTRASOUND BALLOON FOR ENDOSCOPE

CROSS REFERENCE TO RELATED APPLICATION

This application is a continuation application of PCT/JP2014/061982 filed on Apr. 30, 2014 and claims benefit of Japanese Application No. 2013-172473 filed in Japan on Aug. 22, 2013, the entire contents of which are incorporated herein by this reference.

BACKGROUND OF INVENTION

1. Field of the Invention

The present invention relates to an ultrasound endoscope and an ultrasound balloon for an endoscope and, more particularly, to an ultrasound endoscope and an ultrasound balloon for an endoscope in which a balloon is easily detached from a distal end portion of an insertion portion.

2. Description of the Related Art

Conventionally, an ultrasound endoscope has been widely used in a medical field and the like. The ultrasound endoscope obtains ultrasound data through transmission and reception of ultrasound between a distal end portion of an insertion portion and a test target and generates an ultrasound image. A doctor or the like can diagnose the test target in a noninvasive manner looking at the ultrasound image.

In the ultrasound endoscope, an ultrasound probe portion for transmitting and receiving ultrasound is provided at the distal end portion of the insertion portion. In the ultrasound endoscope, a balloon for interposing liquid, for example, water, which is an ultrasound medium for transmitting ultrasound, between an observation target of a subject and the ultrasound probe portion is attached to the distal end portion of the insertion portion. After use of the ultrasound endoscope, the balloon is detached from the distal end portion of the insertion portion.

Conventionally, various proposals concerning balloons of ultrasound endoscopes have been made. Japanese Patent Application Laid-Open Publication No. H07-227393 proposes a technique for, when attaching a balloon to a distal end portion of an insertion portion of an ultrasound endoscope, facilitating the attachment by eliminating a part where air escapes in a storage bag portion.

Japanese Patent Application Laid-Open Publication No. H07-155326 proposes a balloon device for an ultrasound probe that prevents air from being mixed in an inside when an ultrasound transmission medium is encapsulated in a balloon main body.

SUMMARY OF THE INVENTION

An ultrasound endoscope according to an aspect of the present invention comprising: an ultrasound transmitting and receiving portion that is arranged at a distal end portion of an insertion portion, which is inserted into a subject, and transmits and receives ultrasound; a cylindrical balloon closed at a distal end that is arranged to cover the ultrasound transmitting and receiving portion, includes an annular portion at the distal end, and includes a distal end cover portion that closes the annular portion; a first concave groove that is arranged at a distal end of the ultrasound transmitting and receiving portion and in which the annular portion is fit to lock the balloon, the first concave groove being formed over an entire circumference of the ultrasound transmitting and receiving portion; a distal end face that is provided on the distal end side of the ultrasound transmitting and receiving portion to form the first concave groove and covered with the distal end cover portion; and at least one convex portion that is in contact with an inner side surface of the distal end cover portion to increase a frictional force between a surface of the distal end cover portion and a finger, provided on the distal end face to lift at least a part of the distal end cover portion, and has a spherical crown shape.

An ultrasound balloon for an endoscope according to an aspect of the present invention comprising: a cylindrical storing portion that stores an ultrasound medium; a first annular portion that frames a proximal end side of the storing portion and has a Young's modulus larger than a Young's modulus of the storing portion; a second annular portion that frames a distal end side of the storing portion and has a Young's modulus larger than the Young's modulus of the storing portion; and a convex portion that is arranged to close at least a part of the distal end side of the storing portion and includes a convex portion at least on an inner surface or on an outer surface.

DETAILED DESCRIPTION OF THE PREFERRED EMBODIMENT(S)

Embodiments of the present invention are explained below with reference to the drawings.

Note that in respective figures used for the following explanation, in order to show respective components in sizes recognizable on the drawings, scales are varied for each of the components. The present invention is not limited to only numbers of the components, shapes of the components, ratios of sizes of the components, relative positional relations of the respective components shown in these figures.

First Embodiment

Configuration

Figure 1:
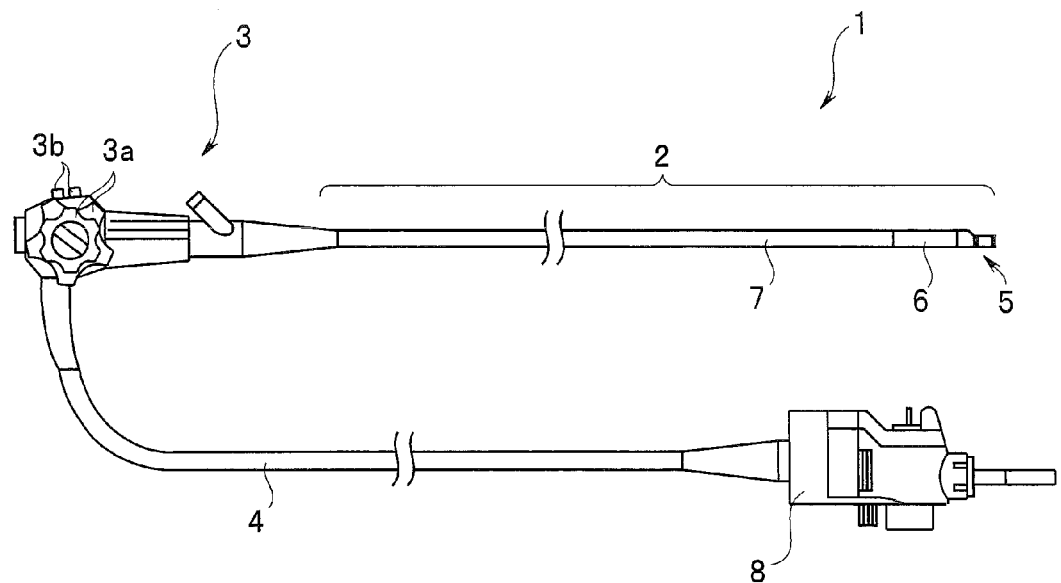
FIG. 1 is an external configuration diagram of an ultrasound endoscope according to a first embodiment of the present invention.

FIG. 1 is an external configuration diagram of an ultrasound endoscope according to a first embodiment of the present invention. An ultrasound endoscope 1 includes an elongated insertion portion 2, an operation portion 3 provided at a proximal end of the insertion portion 2, and a universal cord 4 extending from a side portion of the operation portion 3.

The insertion portion 2 to be inserted into a subject is configured by concatenating a distal end portion 5, a bendable bending portion 6, and a flexible tube portion 7 having flexibility in order from a distal end side. In the operation portion 3, two bending operation knobs 3a and various buttons 3b are provided. A user can bend the bending portion 6 by operating the bending operation knobs 3a and can instruct freeze of an endoscope image, recording of a freeze image, and the like by operating the various buttons 3b.

A distal end of the universal cord 4 is connected to the side portion of the operation portion 3. A scope connector 8 connected to a light source device and an ultrasound observation device not shown in the figure is provided at a proximal end of the universal cord 4.

Figure 2:
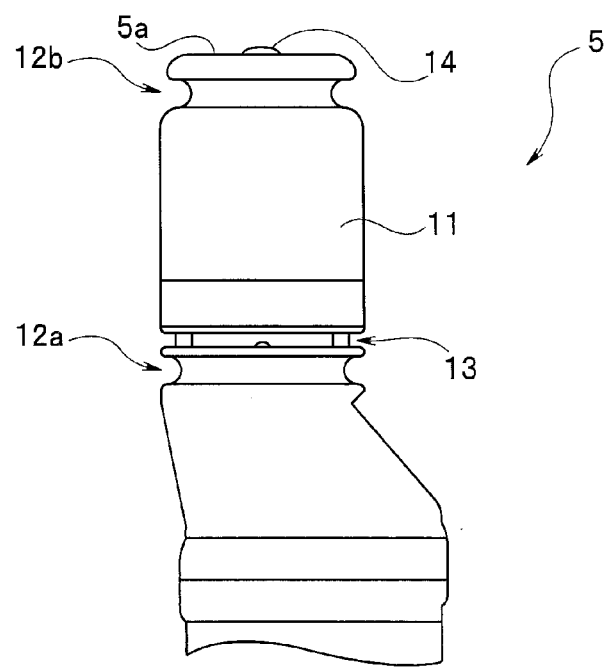
FIG. 2 is a side view of a distal end portion of the ultrasound endoscope not attached with a balloon according to the first embodiment of the present invention.
Figure 3:
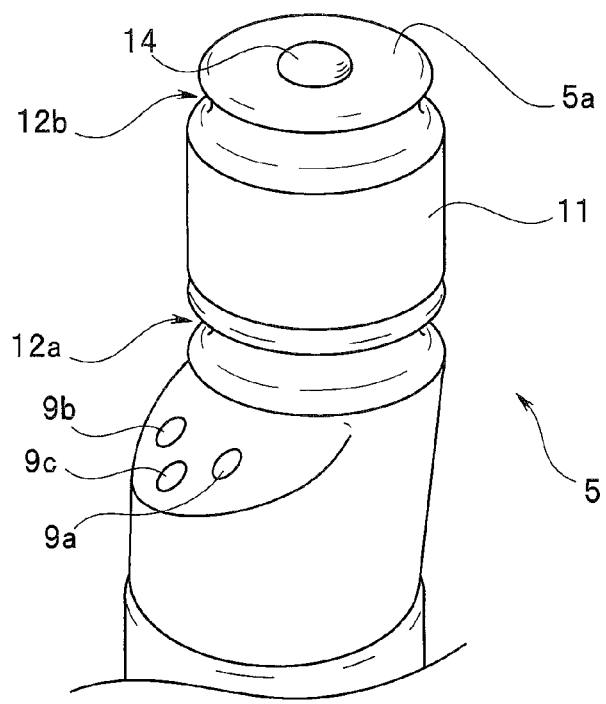
FIG. 3 is a perspective view of the distal end portion of the ultrasound endoscope not attached with the balloon according to the first embodiment of the present invention.

FIG. 2 is a side view of a distal end portion of the ultrasound endoscope not attached with a balloon. FIG. 3 is a perspective view of the distal end portion of the ultrasound endoscope not attached with the balloon. At a distal end portion 5 of the insertion portion 2, an observation window 9a, an illumination window 9b, and a forceps port 9c are provided. Further, as shown in FIG. 2, an ultrasound transducer portion 11 which is an ultrasound transmitting and receiving portion is also provided on a distal end side of the distal end portion 5. The ultrasound transducer portion 11 is an ultrasound probe portion of an electronic radial type. The ultrasound transducer portion 11 includes an acoustic lens made of silicone rubber on an outer surface thereof. The ultrasound transducer portion 11 is arranged at the distal end portion 5 of the insertion portion 2 and configures an ultrasound transmitting and receiving portion including an ultrasound transmitting and receiving surface for transmitting and receiving ultrasound.

Balloon grooves 12a and 12b, which are peripheral grooves, are provided to sandwich the ultrasound transducer portion 11. The balloon groove 12a is provided on a proximal end side of the ultrasound transducer portion 11. The balloon groove 12b is provided on a distal end side of the ultrasound transducer portion 11. That is, the balloon groove 12a is a groove formed between the insertion portion 2 and the ultrasound transducer portion 11 and is a first balloon locking groove for locking a balloon 21 (FIG. 4) that covers the ultrasound transducer portion 11. The balloon groove 12b is a groove formed between the ultrasound transducer portion 11, which is an ultrasound transmitting and receiving portion, and a distal end face 5a of the distal end portion 5 and is a second balloon locking groove for locking the balloon 21 (FIG. 4) that covers the ultrasound transmitting and receiving portion.

On a distal end side of the balloon groove 12a, a water feeding/draining groove 13 for a balloon communicating with an outside is provided. In other words, the balloon grooves 12a and 12b are balloon holding portions for holding a balloon attached to the distal end portion 5 and are recessed grooves formed in a circumferential direction of a columnar distal end portion.

The distal end portion 5 of the insertion portion 2 is arranged on the distal end side with respect to the ultrasound transducer portion 11, which is the ultrasound transmitting and receiving portion, and includes the distal end face 5a disposed spaced apart from the ultrasound transmitting and receiving surface. A convex portion 14 is provided on the distal end face 5a of the distal end portion 5. The convex portion 14 is a portion projecting to the distal end side of the distal end face 5a. As explained below, the convex portion 14 comes into contact with an inner side surface of the balloon attached to the distal end portion 5. In plan view of the distal end face 5a attached with the balloon 21, the distal end face 5a has a circular shape and the convex portion 14 also has a circular shape.

Note that, in FIG. 3, the convex portion 14 is a spherical crown-shaped round projecting portion. However, the convex portion 14 may be a disk-shaped projecting portion. The convex portion 14 does not have a sharp portion at an edge not to damage the balloon when the convex portion 14 is pressed against the inner side surface of the balloon 21.

Figure 4:
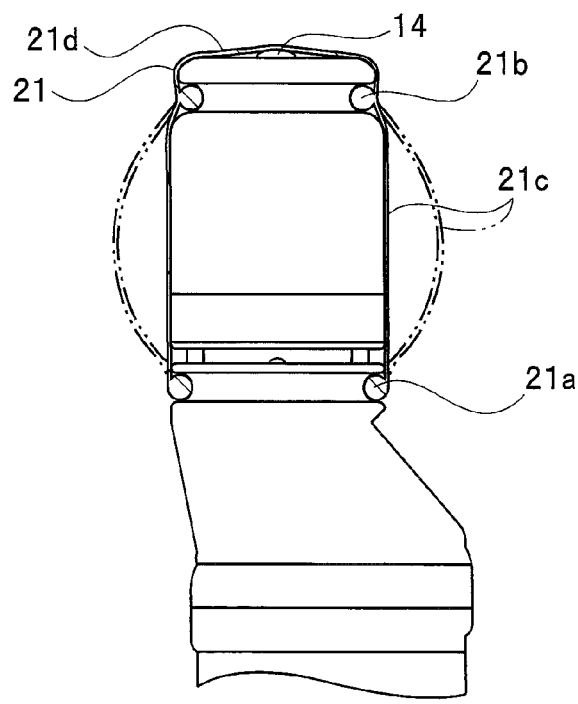
FIG. 4 is a side view of a distal end portion 5 showing a state in which the balloon is attached to the distal end portion 5 according to the first embodiment of the present invention.

FIG. 4 is a side view of the distal end portion 5 showing a state in which the balloon is attached to the distal end portion 5. The balloon 21 is made of an elastic member such as stretchable rubber and has a cylindrical shape closed at a distal end. The balloon 21 includes two elastic ring portions 21a and 21b, which are thick annular portions. The two elastic ring portions 21a and 21b enter the two balloon grooves 12a and 12b of the distal end portion 5 when the balloon 21 is attached to the distal end portion 5.

When the balloon 21 is attached to the distal end portion 5, the elastic ring portion 21a enters the balloon groove 12a on the proximal end side of the distal end portion 5 and adheres to the balloon groove 12a with an elastic force of the elastic ring portion 21a. Similarly, when the balloon 21 is attached to the distal end portion 5, the elastic ring portion 21b enters the balloon groove 12b on the distal end side of the distal end portion 5 and adheres to the balloon groove 12b with an elastic force of the elastic ring portion 21b.

The balloon 21 includes a balloon main body portion 21c between the two elastic ring portions 21a and 21b. The balloon main body portion 21c is a thin cylindrical portion. When liquid is injected into the balloon main body portion 21c, as indicated by alternate long and two short dashes lines in FIG. 4, the balloon main body portion 21c expands. That is, the balloon main body portion 21c configures a cylindrical storing portion that stores an ultrasound medium. The elastic ring portion 21a configures a first annular portion that frames a proximal end side of the balloon main body portion 21c, which is the storing portion, and has a Young's modulus larger than a Young's modulus of the balloon main body portion 21c. The elastic ring portion 21b configures a second annular portion that frames a distal end side of the balloon main body portion 21c, which is the storing portion, and has a Young's modulus larger than the Young's modulus of the balloon main body portion 21c.

The balloon 21 includes, on a distal end side of the elastic ring portion 21a, a distal end cover portion 21d that covers a distal end face of the distal end portion 5. The distal end cover portion 21d is thin and bag-like. The distal end cover portion 21d configures a film portion that closes at least a part of the distal end side of the balloon main body portion 21c, which is the storing portion.

In plan view of the distal end face 5a, a diameter of the circular convex portion 14 is 20% to 80% of a diameter of the circular distal end face 5a. That is, in plan view of the distal end face 5a, the convex portion 14, which is a stress concentrating portion, has a maximum outer diameter of 20 to 80% of the diameter of the distal end face 5a. More preferably, the diameter of the convex portion 14 is 30% to 40% of the diameter of the circular distal end face 5a. If the convex portion 14 has the diameter of this degree, as explained below, stress can be concentrated on the convex portion 14 when the user presses a finger against the convex portion 14 from above the distal end cover portion 21d.

That is, since the convex portion 14 has such a diameter, as explained below, when the user moves the finger in parallel to the distal end face 5a while pushing the convex portion 14 with the finger, stress enough for pulling the balloon 21 in parallel to the distal end face 5a can be concentrated on the convex portion 14. Therefore, the convex portion 14 configures the stress concentrating portion that is provided on the distal end face 5a and on which stress concentrates when the user slides the finger on the distal end face 5a.

Note that, when the convex portion 14 is not circular in plan view of the distal end face 5a, a maximum outer diameter of the convex portion 14 is 20% to 80% and preferably 30% to 40% of the diameter of the circular distal end face 5a. Here, one convex portion 14 is provided. However, a plurality of the convex portions 14 may be provided.

(Action)

Next, action in detaching the balloon 21 from the distal end portion 5 is explained.

Figure 5:
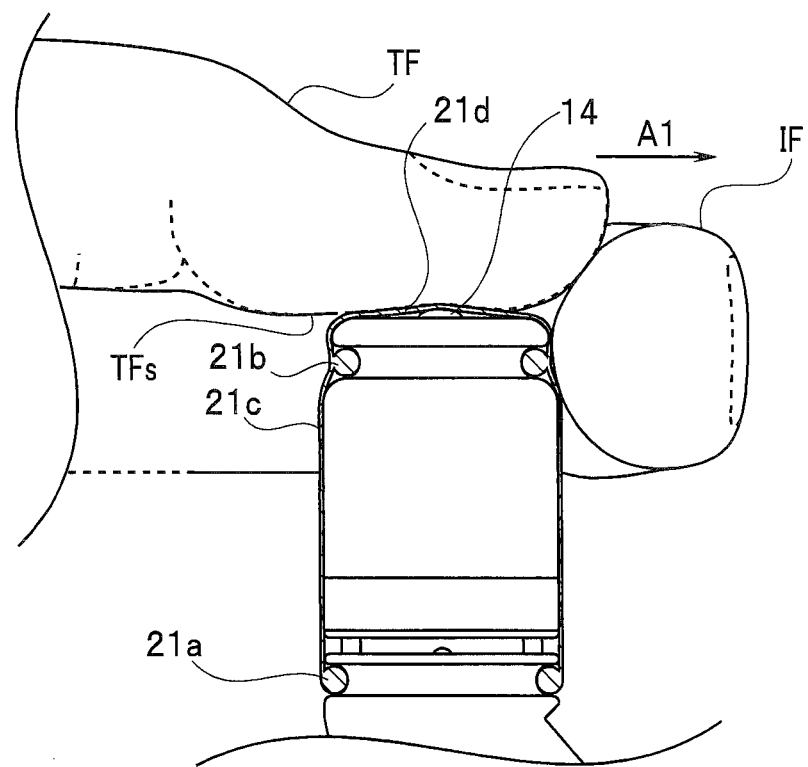
FIG. 5 is a diagram for explaining a state in which fingers are placed on a balloon 21 when the balloon 21 is detached from the distal end portion 5 according to the first embodiment of the present invention.

FIG. 5 to FIG. 8 are diagrams for explaining a state in which the balloon 21 is detached. FIG. 5 is a diagram for explaining a state in which fingers are placed on the balloon 21 when the balloon 21 is detached from the distal end portion 5. As shown in FIG. 5, when detaching the balloon 21 from the distal end portion 5, for example, the user moves a thumb TF in a direction parallel to the distal end face 5a (indicated by an arrow A1) while pushing the distal end cover portion 21d on the convex portion 14 with a pad portion TFs of the thumb TF. Since the finger of the user is covered with a glove, in FIG. 5, the finger is indicated by a dotted line.

When the thumb TF moves while the convex portion 14 of the distal end cover portion 21d is pushed by the pad portion TFs of the thumb TF, a surface of the convex portion 14 is strongly pressed against an inner side surface of the distal end cover portion 21d. Therefore, strong stress is applied to the convex portion 14.

Figure 6:
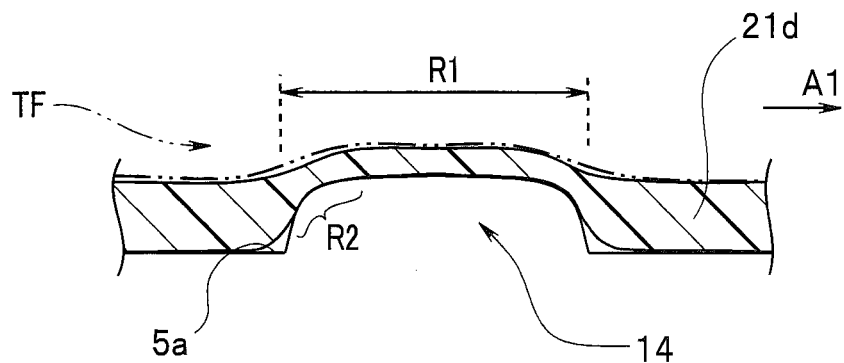
FIG. 6 is a diagram for explaining stress applied to a convex portion 14 according to the first embodiment of the present invention.

FIG. 6 is a diagram for explaining stress applied to the convex portion 14. Since the thumb TF presses the distal end cover portion 21d on the convex portion 14, in FIG. 6, strong stress is applied to a range R1 of the convex portion 14. Further, since the thumb TF moves in the arrow A1 direction, in the range R1, particularly strong stress is applied to a marginal portion R2 on an opposite side of the arrow A1 direction of the convex portion 14.

Figure 7:
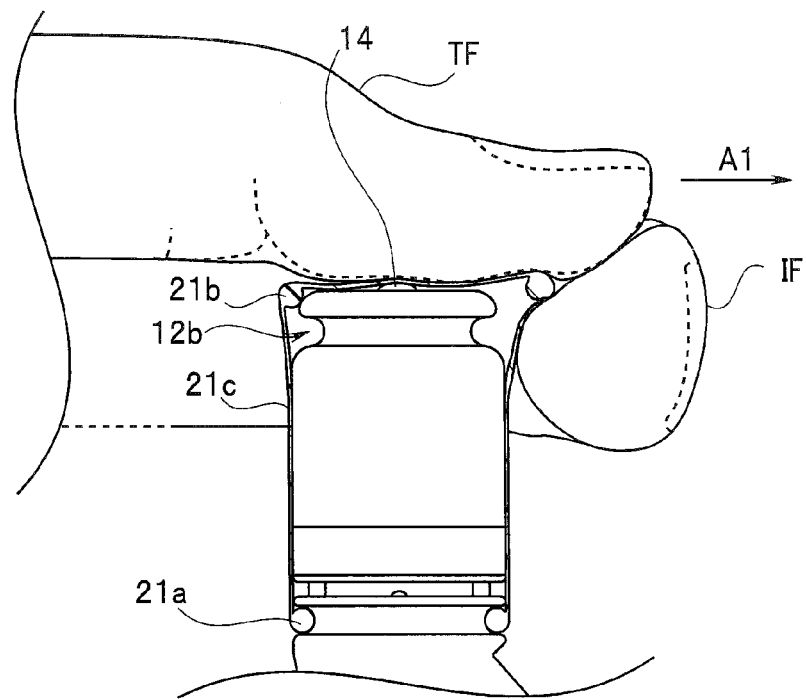
FIG. 7 is a diagram for explaining a state in which a thumb TF moves in a direction of an arrow A1 according to the first embodiment of the present invention.

FIG. 7 is a diagram for explaining a state in which the thumb TF moves in the direction of the arrow A1. The distal end cover portion 21d in the range R1 is squashed by reaction against the strong stress of the convex portion 14. A frictional force between the surface of the distal end cover portion 21d and a surface of the pad portion of the thumb TF increases. Therefore, the distal end cover portion 21d is pulled in the arrow A1 direction according to the movement of the thumb TF.

As shown in FIG. 7, since the distal end cover portion 21d is pulled in the arrow A1 direction, the elastic ring portion 21b on the arrow A1 direction side comes off the balloon groove 12b. Further, when the distal end cover portion 21d is pulled in the arrow A1 direction, the elastic ring portion 21b on the opposite side of the arrow A1 direction also comes off the balloon groove 12b.

When the elastic ring portion 21b comes off the balloon groove 12b, a part of the elastic ring portion 21b can be nipped and pinched by the thumb TF and an index finger IF.

Figure 8:
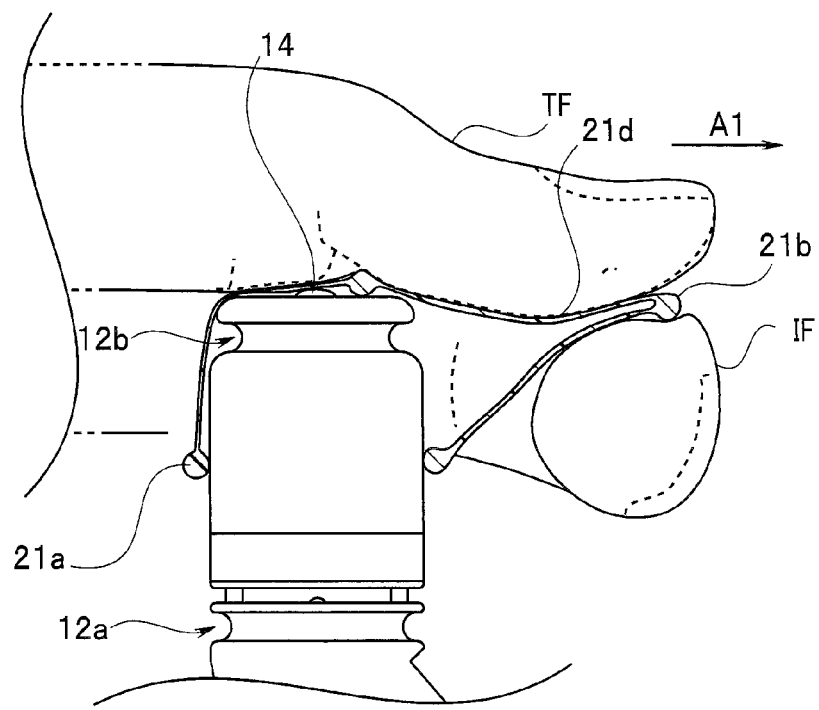
FIG. 8 is a diagram for explaining a state in which a part of an elastic ring portion 21b is pinched by two fingers and the balloon 21 is pulled according to the first embodiment of the present invention.

FIG. 8 is a diagram for explaining a state in which a part of the elastic ring portion 21b is pinched by two fingers and the balloon 21 is pulled. As shown in FIG. 8, when the elastic ring portion 21b is pinched and pulled, the elastic ring portion 21a also comes off the balloon groove 12a.

As explained above, since the convex portion 14 is provided on the distal end face 5a of the distal end portion 5, when the user moves the finger in parallel to the distal end face 5a while pushing the convex portion 14 with the finger from above the distal end cover portion 21d of the balloon 21, a frictional force between the surface of the distal end cover portion 21d and the thumb TF increases because of the reaction of the convex portion 14 to which stress stronger than stress applied to other portions of the distal end face 5a is applied. Therefore, when the thumb TF is moved in the direction parallel to the distal end face 5a of the distal end portion 5, the distal end cover portion 21d is pulled by the thumb TF.

As a result, the elastic ring portion 21b comes off the balloon groove 12b. Subsequently, the elastic ring portion 21a also comes off the balloon groove 12a.

Therefore, according to the present embodiment, the user can easily detach the balloon from the distal end portion of the insertion portion.

Next, modifications of the first embodiment are explained.

The ultrasound endoscope 1 of the first embodiment includes the convex portion 14 on the distal end face 5a of the distal end portion 5 of the insertion portion 2. An ultrasound endoscope of a first modification includes a groove 15 on the distal end face 5a of the distal end portion 5. A balloon 22 used in the modification 1 is cylindrical and does not include a distal end cover portion that covers the distal end face 5a of the distal end portion 5.

Figure 9:
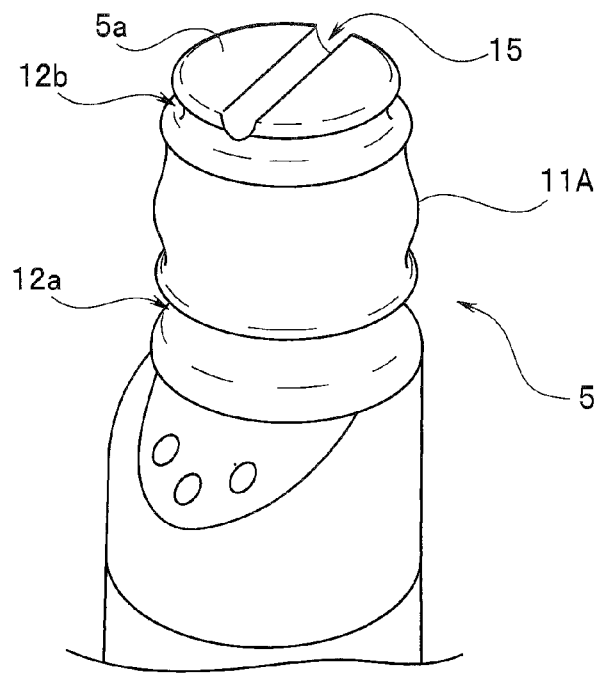
FIG. 9 is a perspective view of the distal end portion 5 of an ultrasound endoscope 1 according to a modification 1 of the first embodiment of the present invention.
Figure 10:
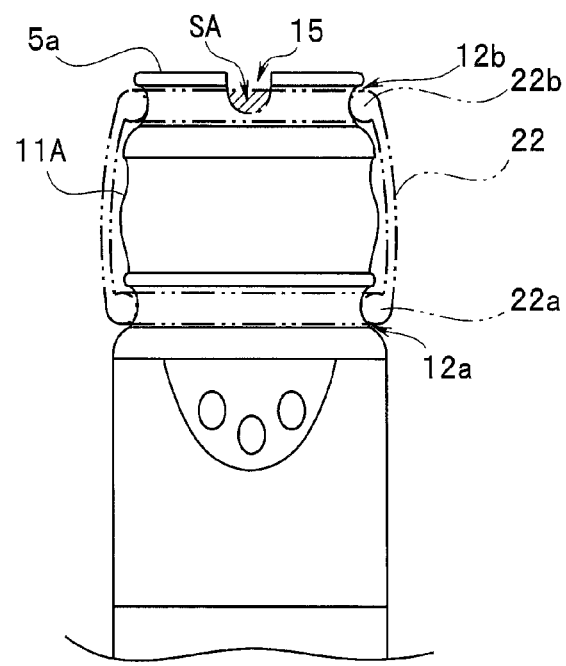
FIG. 10 is a front view of the distal end portion 5 of the ultrasound endoscope 1 according to the modification 1 of the first embodiment of the present invention.

FIG. 9 is a perspective view of the distal end portion 5 of the ultrasound endoscope 1 according to the modification 1. FIG. 10 is a front view of the distal end portion 5 of the ultrasound endoscope 1 according to the modification 1. Note that, here, a sectional shape of a surface of an ultrasound transducer portion 11A taken along an axial direction the distal end portion 5 is a convex curved surface in a center portion.

The groove 15 having a linear shape is formed on the distal end face 5a of the distal end portion 5. The groove 15 is formed from one end of the distal end face 5a of the distal end portion 5 to the other end through a center of the circular distal end face 5a. The distal end portion 5 has a slitting shape. That is, the groove 15, which is a stress concentrating portion, is a groove having a center axis on a straight line and traversing the distal end face.

Note that, here, one groove 15 is formed. However, a plurality of the grooves 15 may be formed.

As shown in FIG. 10, the groove 15 has depth from the distal end face 5a up to halfway in the balloon groove 12b. Therefore, when the balloon 22 is attached to the distal end portion 5 and an elastic ring portion 22b on the distal end side of the balloon 22 indicated by an alternate long and two short dashes line enters the balloon groove 12b, both end portions of the groove 15 are partially covered by a part of the elastic ring portion 22b. That is, as shown in FIG. 10, a portion SA indicated by hatching at an end portion of the groove 15 is covered by the elastic ring portion 22b.

Figure 11:
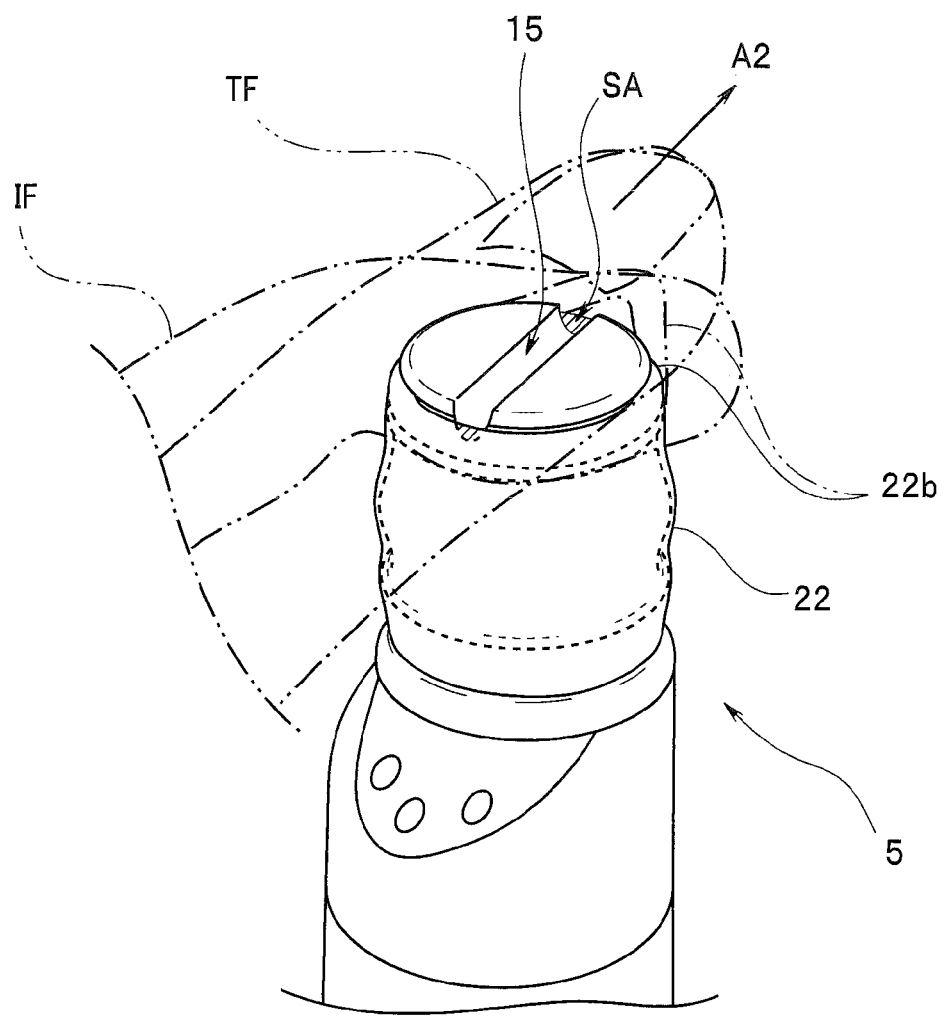
FIG. 11 is a perspective view of the distal end portion 5 for explaining detachment of a balloon 22 in a case of the modification 1 of the first embodiment of the present invention.
Figure 12:
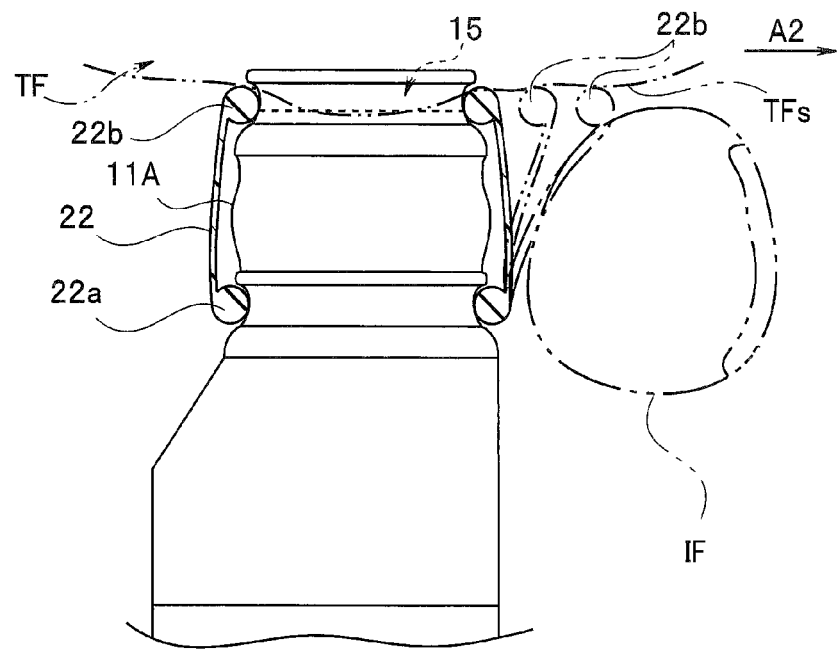
FIG. 12 is a front view for explaining the detachment of the balloon 22 in the case of the modification 1 of the first embodiment of the present invention.

FIG. 11 is a perspective view of the distal end portion 5 for explaining detachment of the balloon 22 in a case of this modification 1. FIG. 12 is a front view for explaining the detachment of the balloon 12 in the case of this modification 1.

In a state in which the user places the thumb TF on the groove 15, when the user presses the pad portion TFs of the thumb TF against the groove 15, stress concentrates on marginal portions of the groove 15. Therefore, the pad portion TFs of the thumb TF is deformed and a part of the pad portion TFs enters the groove 15. That is, the marginal portions of the groove 15 configure stress concentrating portions. When the user slides the thumb TF on the distal end face 5a along the axial direction of the groove 15 in that state, a portion where the elastic ring portion 22b is exposed in the portion SA at the end portion of the groove 15 is pushed by the pad portion TFs.

As a result, as indicated by alternate long and two short dashes lines in FIG. 11 and FIG. 12, as the pad portion TFs of the thumb TF moves in an arrow A2 direction, an elastic ring portion 22a is pulled by the pad portion TFs to extend in an outer diameter direction and is deformed such that the elastic ring portion 22a can be pinched by the index finger IF and the thumb TF.

Note that, in this modification 1, the balloon 22 is cylindrical. However, the balloon 22 may be a cylindrical body closed at a distal end like the balloon 21 explained in the first embodiment.

In this case, a lower limit of width of the groove 15 in plan view of the distal end face 5a is 30% to 50% of the diameter of the circular distal end face 5a. More preferably, the width of the groove 15 is 30% to 40% of the diameter of the circular distal end face 5a. An upper limit of the width of the groove 15 is a diameter enough for edge portions to be formed at the marginal portions of the groove 15.

Further, in the modification 1 explained above, the finger is moved along the groove 15 to push out the elastic ring portion 22a in the outer diameter direction. However, the elastic ring portion 22a may be pushed out in the outer diameter direction by an instrument such as tweezers.

Therefore, according to this modification 1, as in the first embodiment, the user can easily detach the balloon from the distal end portion of the insertion portion.

Next, a second modification is explained. An ultrasound endoscope of the second modification includes a concave portion 16 on the distal end face 5a of the distal end portion 5. Like the balloon 21 of the first embodiment explained above, the balloon 21 used in this modification 2 includes the distal end cover portion 21d that covers the distal end face 5a of the distal end portion 5.

Figure 13:
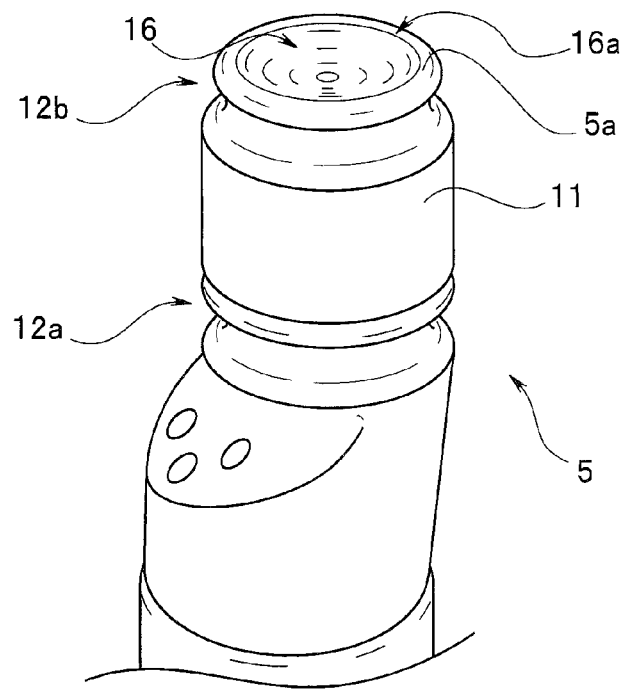
FIG. 13 is a perspective view of the distal end portion 5 of the ultrasound endoscope 1 according to a modification 2 of the first embodiment of the present invention.

FIG. 13 is a perspective view of the distal end portion 5 of the ultrasound endoscope 1 according to the modification 2. The concave portion 16 is formed on the distal end face 5a of the distal end portion 5. The distal end cover portion 21d of the balloon 21 is arranged to cover the concave portion 16 when the balloon 21 is attached to the distal end portion 5. A sectional shape of the concave portion 16 taken along an axis of the distal end portion 5 is a tapered shape or a bowl shape.

Figure 14:
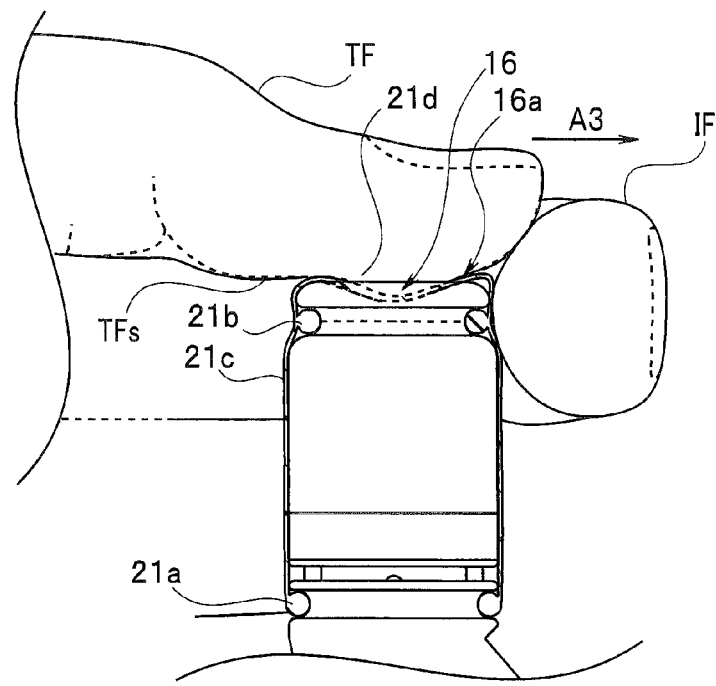
FIG. 14 is a diagram for explaining a state in which fingers are placed on the balloon 21 when the balloon 21 is detached from the distal end portion 5 according to the modification 2 of the first embodiment of the present invention.

Next, action of the modification 2 is explained. FIG. 14 is a diagram for explaining a state in which fingers are placed on the balloon 21 when the balloon 21 is detached from the distal end portion 5. As shown in FIG. 14, when detaching the balloon 21 from the distal end portion 5, for example, the user moves, that is, slides the thumb TF in the direction parallel to the distal end face 5a (indicated by the arrow A1) while pushing the distal end cover portion 21d on the concave portion 16 with the pad portion TFs of the thumb TF. Since the finger of the user is covered by a glove, in FIG. 14, the finger is indicated by a dotted line.

When the thumb TF moves while a concave portion 16 of the distal end cover portion 21d is pushed by the pad portion TFs of the thumb TF, a peripheral portion 16a of the concave portion 16 is strongly pressed against an inner surface of the distal end cover portion 21d. Therefore, stronger stress is applied to the peripheral portion 16a of the concave portion 16 than other portions of the concave portion 16.

Figure 15:
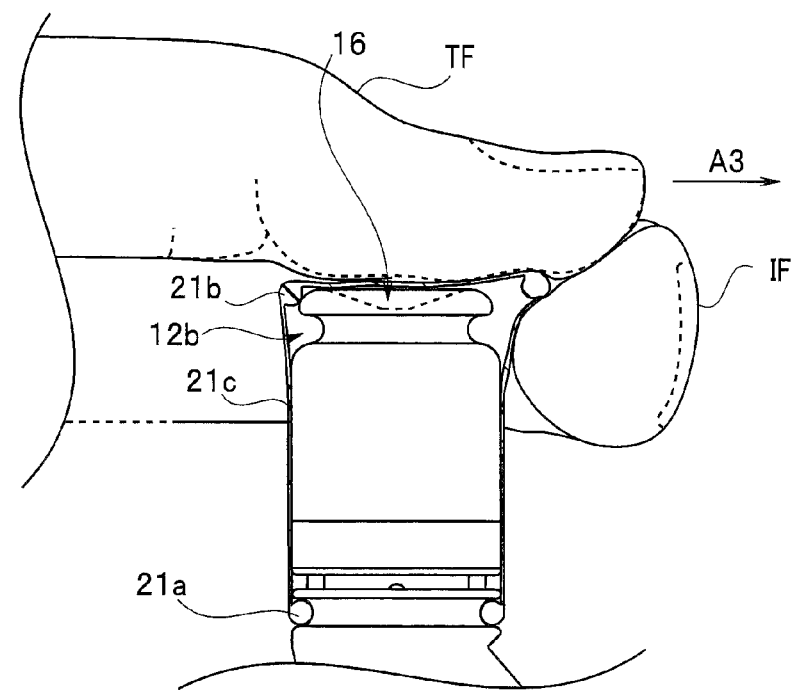
FIG. 15 is a diagram for explaining a state in which the thumb TF moves in a direction of an arrow A3 according to the modification 2 of the first embodiment of the present invention.

FIG. 15 is a diagram for explaining a state in which the thumb TF moves in a direction of an arrow A3. A frictional force between the surface of the distal end cover portion 21*d* and the surface of the pad portion of the thumb TF increases because of reaction against the strong stress of the peripheral portion 16*a* of the concave portion 16. Therefore, the distal end cover portion 21*d* is pulled in the arrow A3 direction according to the movement of the thumb TF.

As shown in FIG. 15, since the distal end cover portion 21*d* is pulled in the arrow A3 direction, the elastic ring portion 21*b* on the arrow A1 direction side comes off the balloon groove 12*b*. When the distal end cover portion 21*d* is further pulled in the arrow A3 direction, the elastic ring portion 21*b* on an opposite side of the arrow A3 direction also comes off the balloon groove 12*b*.

When the elastic ring portion 21*b* comes off the balloon groove 12*b*, a part of the elastic ring portion 21*b* can be nipped and pinched by the thumb TF and the index finger IF.

A lower limit of a diameter of the circular concave portion 16 in plan view of the distal end face 5*a* is 20% to 50% of the diameter of the circular distal end face 5*a*. That is, in plan view of the distal end face 5*a*, the concave portion 16, which is a stress concentrating portion, has a maximum outer diameter equal to or larger than 20% of the diameter of the distal end face 5*a*. More preferably, the diameter of the concave portion 16 is 30% to 40% of the diameter of the circular distal end face 5*a*. An upper limit of the diameter of the concave portion 16 is a diameter enough for an edge portion to be formed at an outer marginal portion of the concave portion 16.

Note that, when the concave portion 16 in plan view of the distal end face 5*a* is not circular, a maximum outer diameter of the concave portion 16 is 20% to 50% and preferably 30% to 40% of the diameter of the circular distal end face 5*a*.

Therefore, according to this modification 2, as in the first embodiment, the user can easily detach the balloon from the distal end portion of the insertion portion.

Figure 16:
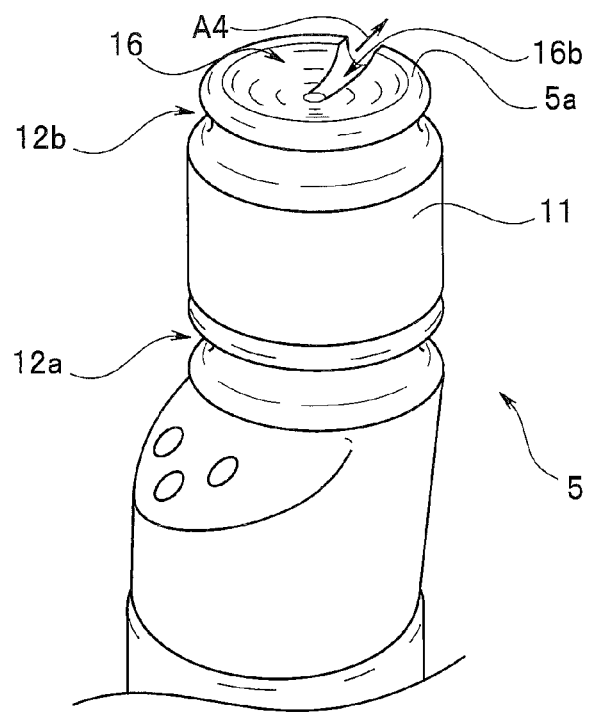
FIG. 16 is a perspective view of the distal end portion 5 of the ultrasound endoscope 1 in which a groove 16b is provided in a part of a concave portion 16 according to a modification 3 of the first embodiment of the present invention.

Note that a groove 16*b* may be provided in a part of the concave portion 16. FIG. 16 is a perspective view of the distal end portion 5 of the ultrasound endoscope 1 according to a modification 3 in which the groove 16*b* is provided in a part of the concave portion 16.

As shown in FIG. 16, in a part of the concave portion 16, the groove 16*b* extending from a center portion of the concave portion 16 toward an outer diameter direction orthogonal to the axial direction of the distal end portion 5 is formed. Other components of this modification 3 are the same as the components of the modification 2 explained above.

Figure 17:
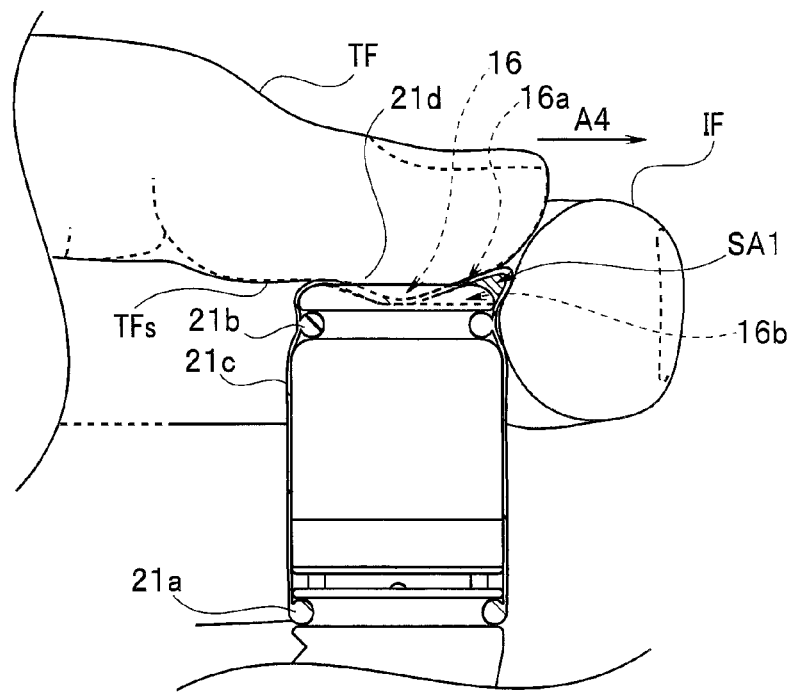
FIG. 17 is a diagram for explaining a state in which a finger is placed on the balloon 21 when the balloon 21 is detached from the distal end portion 5 according to the modification 3 of the first embodiment of the present invention.

Next, action of this modification 3 is explained. FIG. 17 is a diagram for explaining a state in which a finger is placed on the balloon 21 when the balloon 21 is detached from the distal end portion 5. As shown in FIG. 17, when detaching the balloon 21 from the distal end portion 5, for example, the user moves, that is, slides the thumb TF in the direction parallel to the distal end face 5*a* and a direction of the groove 16*b* (indicated by an arrow A4) while pushing the distal end cover portion 21*d* on the concave portion 16 with the pad portion TFs of the thumb TF.

When the thumb TF moves on the distal end face 5*a* while the concave portion 16 of the distal end cover portion 21*d* is pushed by the pad portion TFs of the thumb TF, the peripheral portion 16*a* of the concave portion 16 is strongly pressed against the inner surface of the distal end cover portion 21*d*. Air or liquid in the distal end cover portion 21*d* is pushed out in the outer diameter direction of the distal end portion 5 along the groove 16*b*. As a result, as shown in FIG. 17, strong stress is applied to the peripheral portion 16*a* of the concave portion 16. Therefore, the distal end cover portion 21*d* is pulled in the arrow A4 direction. The air or the liquid present in the concave portion 16 is pushed out to a portion SA1 indicated by hatching.

Thereafter, as shown in FIG. 15, a portion (the portion SA1 indicated by hatching) of the distal end cover portion 21*d* including the air or the liquid can be pinched by the thumb TF and the index finger IF. Therefore, the distal end cover portion 21*d* is pulled in the arrow A4 direction. The elastic ring portions 21*a* and 21*b* on the arrow A4 direction side respectively come off the balloon grooves 12*a* and 12*b*.

Therefore, according to this modification 3, as in the first embodiment, the user can easily detach the balloon from the distal end portion of the insertion portion.

Second Embodiment

In the first embodiment, the stress concentrating portion is provided at the distal end portion of the insertion portion of the ultrasound endoscope. However, in a second embodiment, a stress concentrating portion is provided in a balloon.
(Configuration)

Figure 18:
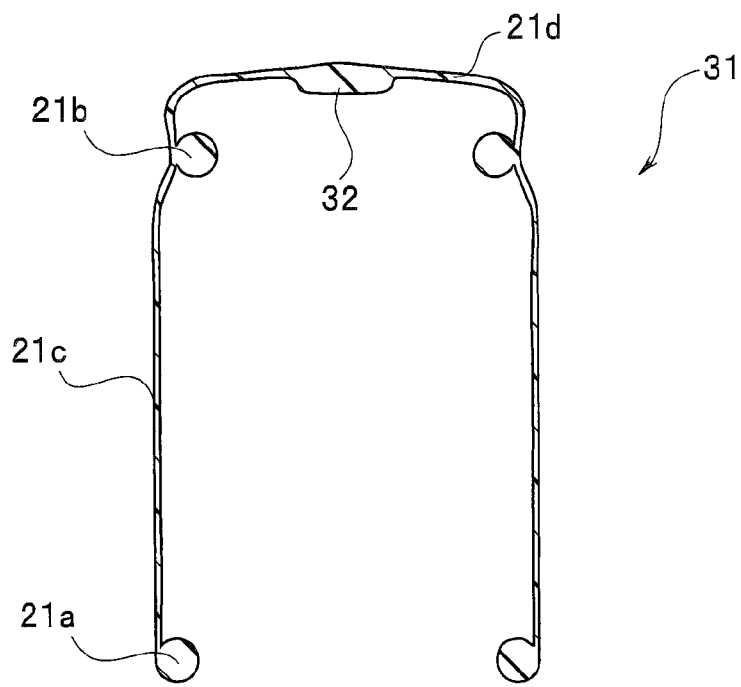
FIG. 18 is a sectional view of a balloon according to a second embodiment of the present invention.

FIG. 18 is a sectional view of a balloon according to the second embodiment of the present invention. A configuration of an ultrasound endoscope attached with the balloon of the present embodiment is the same as a configuration of the ultrasound endoscope 1 of the first embodiment. Therefore, same components are denoted by same reference numerals and signs and explanation of the components is omitted.

As shown in FIG. 18, a balloon 31 is made of an elastic member such as stretchable rubber and has a cylindrical shape closed at a distal end. The balloon 31 has a configuration substantially the same as a configuration of the balloon 21 of the first embodiment. Therefore, same components are denoted by same reference numerals and signs. Different components are mainly explained.

The balloon 31 includes the two elastic ring portions 21*a* and 21*b*, which are thick annular portions. The elastic ring portions 21*a* and 21*b* enter the two balloon grooves 12*a* and 12*b* of the distal end portion 5 when the balloon 31 is attached to the distal end portion 5.

When the balloon 31 is attached to the distal end portion 5, the elastic ring portion 21*a* enters the balloon groove 12*a* on the proximal end side of the distal end portion 5 and adheres to the balloon groove 12*a* with an elastic force of the elastic ring portion 21*a*. Similarly, when the balloon 21 is attached to the distal end portion 5, the elastic ring portion 21*b* enters the balloon groove 12*b* on the distal end side of the distal end portion 5 and adheres to the balloon groove 12*b* with an elastic force of the elastic ring portion 21*b*.

The balloon 31 includes the balloon main body portion 21*c* between the two elastic ring portions 21*a* and 21*b*. The balloon main body portion 21*c* is a thin cylindrical portion. When liquid is injected into the balloon main body portion 21*c*, the balloon main body portion 21*c* expands. That is, the balloon main body portion 21*c* is a cylindrical storing portion that stores an ultrasound medium. The elastic ring portion 21*a* configures a first annular portion that frames the proximal end side of the balloon main body portion 21*c*, which is the storing portion, and has a Young's modulus larger than a Young's modulus of the balloon main body portion 21*c*. The elastic ring portion 21*b* configures a second annular portion that frames a distal end side of the balloon main body portion 21*c*, which is the storing portion, and has a Young's modulus larger than the Young's modulus of the balloon main body portion 21*c*.

The balloon 31 includes, on a distal end side of the elastic ring portion 21b, the thin and bag-like distal end cover portion 21d that covers the distal end face of the distal end portion 5. The distal end cover portion 21d configures a film portion that closes at least a part of the distal end side of the balloon main body portion 21c, which is the storing portion. A part (here, a center portion) of the distal end cover portion 21d includes a convex portion 32 projecting to an inner surface side of the balloon 31.

(Action)

When detaching the balloon 31 attached to the distal end portion 5, a user moves, that is, slides the thumb TF in the direction parallel to the distal end face 5a while pushing the distal end cover portion 21d with the thumb TF.

Figure 19:
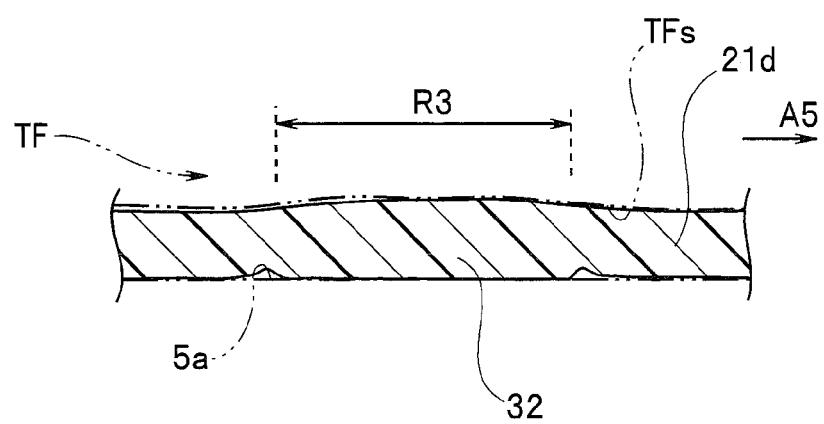
FIG. 19 is a partial sectional view of a distal end cover portion 21d for explaining a state in which a surface of the distal end cover portion 21d is pressed by the thumb TF according to the second embodiment of the present invention.

FIG. 19 is a partial sectional view of the distal end cover portion 21d for explaining a state in which the surface of the distal end cover portion 21d is pressed by the thumb TF. Since the pad portion TFs of the thumb TF presses the surface of the distal end cover portion 21d, the convex portion 32 is compressed. Since the convex portion 32 is compressed, a frictional force between the surface of the pad portion TFs of the thumb TF and the surface of the distal end cover portion 21d increases. In FIG. 19, a frictional force in a range R3 is large.

When the thumb TF moves in an arrow A5 direction while the convex portion 32 of the distal end cover portion 21d is pushed by the pad portion TFs of the thumb TF, strong stress is applied to the convex portion 32 in the range R3 shown in FIG. 19.

Figure 20:
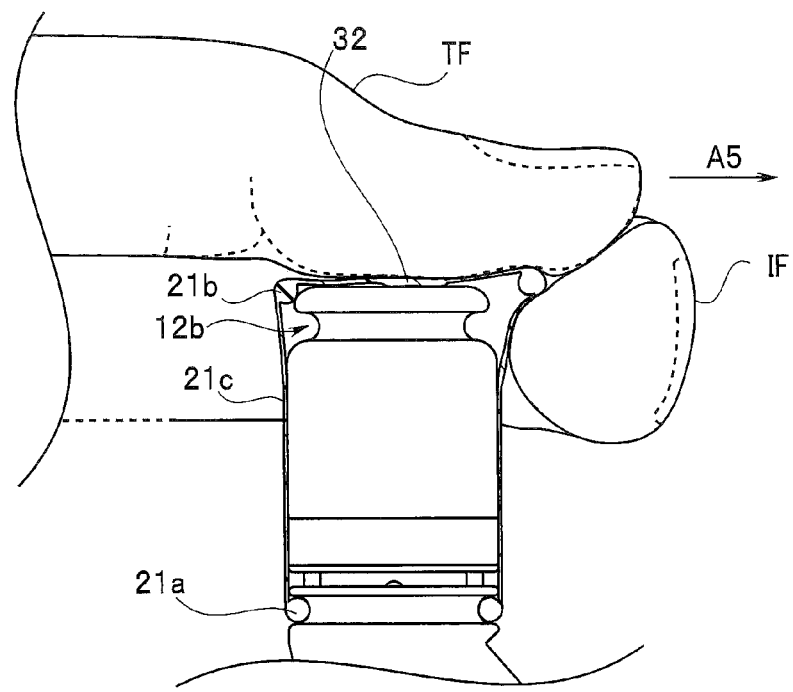
FIG. 20 is a diagram for explaining a state in which the thumb TF moves in a direction of an arrow A5 according to the second embodiment of the present invention.

FIG. 20 is a diagram for explaining a state in which the thumb TF moves in an arrow A5 direction. As shown in FIG. 20, when detaching the balloon 31 from the distal end portion 5, for example, the user moves, that is, slides the thumb TF in the direction parallel to the distal end face 5a (the arrow A5 direction) while pushing the distal end cover portion 21d on the convex portion 32 with the pad portion TFs of the thumb TF. Note that, since the finger of the user is covered by a glove, in FIG. 20, the finger is indicated by a dotted line.

The convex portion 32 in the range R3 is squashed by the thumb TF and a frictional force between the surface of the distal end cover portion 21d and the surface of the pad portion TFs of the thumb TF increases. Therefore, the distal end cover portion 21d is pulled in the arrow A5 direction according to the movement of the thumb TF.

Therefore, as shown in FIG. 20, the distal end cover portion 21d is pulled in the arrow A5 direction. Therefore, the elastic ring portion 21b on the arrow A5 direction side comes off the balloon groove 12b. When the distal end cover portion 21d is further pulled in the arrow A5 direction, a part of the elastic ring portion 21b can be nipped and pinched by the thumb TF and the index finger IF.

Figure 21:
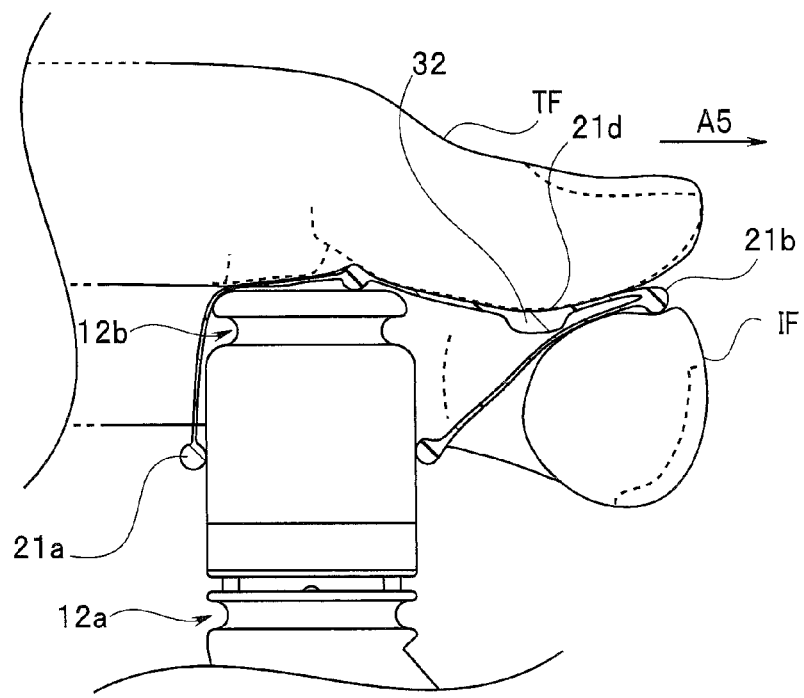
FIG. 21 is a diagram for explaining a state in which a part of the elastic ring portion 21b is pinched by two fingers and the balloon 21 is pulled according to the second embodiment of the present invention.

FIG. 21 is a diagram for explaining a state in which a part of the elastic ring portion 21d is pinched by two fingers and the balloon 21 is pulled. As shown in FIG. 21, when the elastic ring portion 21b is pinched and pulled, the elastic ring portion 21a also comes off the balloon groove 12a.

As explained above, the convex portion 32 is provided on an inner side of the distal end cover portion 21d of the balloon 31. Therefore, when the user moves the finger in parallel to the distal end face 5a while pushing the convex portion 32 of the distal end cover portion 21d of the balloon 31 with the finger, frictional force between the surface of the distal end cover portion 21d and the surface of the pad portion TFs of the thumb TF increases because of the convex portion 32. Therefore, when the thumb TF is moved in the direction parallel to the distal end face 5a of the distal end portion 5, the distal end cover portion 21d is also pulled by the thumb TF.

As a result, the elastic ring portion 21b comes off the balloon groove 12b. Subsequently, the elastic ring portion 21a also comes off the balloon groove 12a.

Note that, when the balloon 31 shown in FIG. 18 is attached to the distal end portion 5, a shape of the distal end face 5a of the distal end portion 5 may be, for example, a concave portion shape shown in FIG. 13. When the distal end face 5a has the concave portion shape, during use of the ultrasound endoscope 1, a portion of the convex portion 32 of the distal end cover portion 21d does not project to the distal end side. As a result, there is an effect that, when the insertion portion 2 is inserted, a projection of the convex portion 32 does not obstruct an inserting motion.

Therefore, according to the present embodiment, the user can easily detach the balloon from the distal end portion of the insertion portion.

Next, modifications of the second embodiment are explained.

The balloon 31 of the second embodiment includes the convex portion 32 on the inner surface side of the distal end cover portion 21d. However, a balloon of a first modification includes a convex portion 32a on an outer surface of the distal end cover portion 21d. A balloon 31A used in this modification 1 is different from the balloon 31 explained above only in that the balloon 31A includes the convex portion 32a on the outer surface of the distal end cover portion 21d. Other components are the same as the components of the balloon 31.

Figure 22:
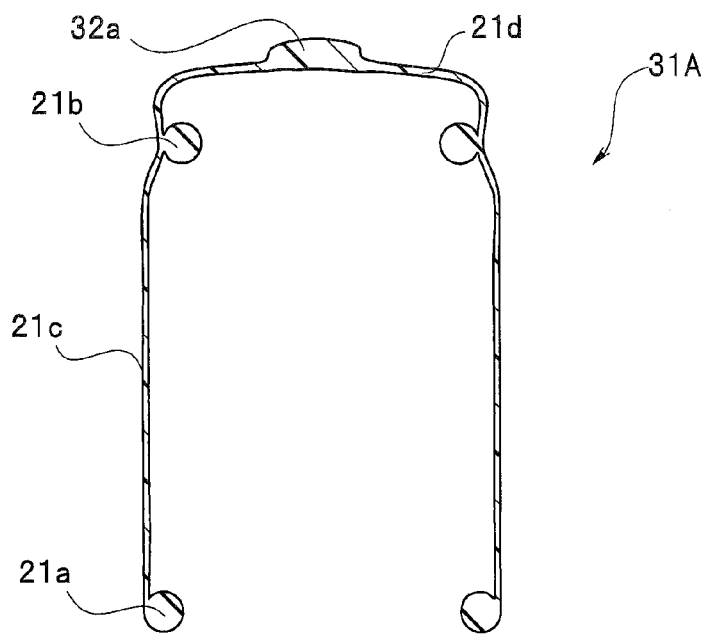
FIG. 22 is a sectional view of a balloon 31A taken along an axial direction of the cylindrical balloon 31A according to a modification 1 of the second embodiment of the present invention.

FIG. 22 is a sectional view of the balloon 31A of the modification 1 taken along an axial direction of the cylindrical balloon 31A.

The convex portion 32a is provided on the outer surface of the distal end cover portion 21d. However, the action of the convex portion 32a is the same as the action of the convex portion 32 explained above. That is, when the user moves the finger in parallel to the distal end face 5a while pushing the convex portion 32a of the distal end cover portion 21d of the balloon 31 with the finger, a frictional force between the surface of the distal end cover portion 21d and the surface of the pad portion TFs of the thumb TF increases because of the convex portion 32a. Therefore, when the thumb TF is moved in the direction parallel to the distal end face 5a of the distal end portion 5, the distal end cover portion 21d is also pulled by the thumb TF.

As a result, the elastic ring portion 21b comes off the balloon groove 12b. Subsequently, the elastic ring portion 21a also comes off the balloon groove 12a.

Therefore, according to this modification 1, as in the second embodiment, the user can easily detach the balloon from the distal end portion of the insertion portion.

Note that convex portions may be present both on the outer surface and on the inner surface of the distal end cover portion 21d.

The balloon 31 of the second embodiment includes the convex portion 32 on the inner side of the distal end cover portion 21d. However, a balloon of a second modification includes a convexo-concave portion 33 on an outer surface side surface of the distal end cover portion 21d. A balloon 31B used in this modification 2 is different from the balloon 31 explained above only in that the balloon 31B includes the convexo-concave portion 33 on an outer side of the distal end cover portion 21d instead of the convex portion 32. Other components are the same as the components of the balloon 31.

Figure 23:
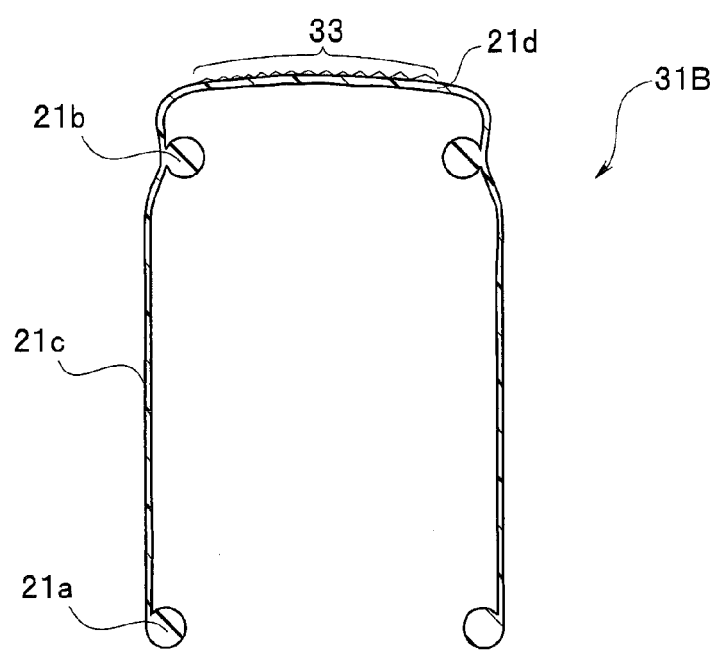
FIG. 23 is a sectional view of a balloon 31B taken along an axial direction of the cylindrical balloon 31B according to the modification 1 of the second embodiment of the present invention.

FIG. 23 is a sectional view of the balloon 31B of the modification 2 taken along an axial direction of the cylindrical balloon 31B.

The convexo-concave portion 33 is provided on the outer surface of the distal end cover portion 21d. Action of the convexo-concave portion 33 is the same as the action of the convex portion 32 explained above. That is, when the user moves the finger in parallel to the distal end face 5a while pushing the convexo-concave portion 33 of the distal end cover portion 21d of the balloon 31B with the finger, a frictional force between the surface of the distal end cover portion 21d and the surface of the pad portion TFs of the thumb TF increases because of the convexo-concave portion 33. Therefore, when the thumb TF is moved in the direction parallel to the distal end face 5a of the distal end portion 5, the distal end cover portion 21d is also pulled by the thumb TF.

Note that the convexo-concave portion 33 may be a rough surface including a plurality of convexo-concavities.

As a result, the elastic ring portion 21b comes off the balloon groove 12b. Subsequently, the elastic ring portion 21a also comes off the balloon groove 12a.

Therefore, according to this modification 2, as in the second embodiment, the user can easily detach the balloon from the distal end portion of the insertion portion.

As explained above, according to the respective embodiments and the respective modifications explained above, it is possible to provide an ultrasound endoscope and an ultrasound balloon for an endoscope in which a balloon is easily detached from a distal end portion of an insertion portion even after use of the ultrasound endoscope.

Note that, in the respective embodiments and the respective modifications explained above, the ultrasound transmitting and receiving portion is a radial type. However, the ultrasound transmitting and receiving portion may be a convex type.

The present invention is not limited to the embodiments explained above. Various changes, alternations, and the like are possible in a range in which a gist of the present invention is not changed.

What is claimed is:

1. An ultrasound endoscope comprising:
   an ultrasound transmitting and receiving portion that is arranged at a distal end portion of an insertion portion configured to be inserted into a subject, the ultrasound transmitting and receiving portion having an ultrasound transmitting and receiving surface that transmits and receives ultrasound in a direction perpendicular to a longitudinal axis direction of the insertion portion;
   a cylindrical balloon configured to be closed at a distal end and to cover the ultrasound transmitting and receiving portion, the cylindrical balloon including a first annular portion provided at the distal end, a second annular portion provided to be proximal with respect to the first annular portion, and a distal end cover portion configured to close the first annular portion;
   a first concave groove that is arranged at a distal end of the ultrasound transmitting and receiving portion and in which the annular portion is fit to lock the balloon, the first concave groove being formed over an entire circumference of the ultrasound transmitting and receiving portion;
   a second concave groove that is arranged to be proximal with respect to the first concave groove and in which the second annular portion is fit to lock the balloon, the second concave groove being formed over the entire circumference of the ultrasound transmitting and receiving portion;
   a circular distal end face that is provided on a distal end side of the ultrasound transmitting and receiving portion to be spaced apart from the ultrasound transmitting and receiving surface to form the first concave groove, the distal end face being provided to be distal with respect to a virtual surface perpendicular to the longitudinal axis direction at a position of the first concave groove, and being covered with the distal end cover portion; and
   at least one convex portion that has a spherical crown shape and is provided on the distal end face to project to a distal end side of the distal end face, the convex portion being in contact with an inner side surface of the distal end cover portion when the cylindrical balloon is attached to the distal end portion of the insertion portion;
   wherein an outer surface of the distal end cover portion is adapted to be pushed by a finger to increase a frictional force between the outer surface of the distal end cover portion and the finger by reaction against stress by the finger.

2. The ultrasound endoscope according to claim 1, wherein the convex portion has a maximum outer diameter of 20 to 80% of a diameter of the distal end face in a plan view of the distal end face as viewed in the longitudinal axis direction of the insertion portion.

* * * * *